United States Patent [19]

Asai et al.

[11] 4,202,905

[45] May 13, 1980

[54] LUMINOUS MATERIAL FOR USE IN FISHERY AND METHOD FOR THE PRODUCTION THEREOF

[75] Inventors: Yoshiyuki Asai, Yokohama; Nobuyoshi Makiguchi, Fujsawa; Masanobu Arita; Mitsuyoshi Nakamura, both of Kamakura; Kozo Sasa, Yokohama, all of Japan

[73] Assignee: Mitsui Toatsu Chemicals Incorporated, Tokyo, Japan

[21] Appl. No.: 880,163

[22] Filed: Feb. 22, 1978

[51] Int. Cl.$^2$ .............................................. A23L 1/325
[52] U.S. Cl. ........................................ 426/1; 426/240; 435/178; 435/179; 435/182
[58] Field of Search ..................... 426/1, 2, 3, 240, 89; 195/59

[56] References Cited

U.S. PATENT DOCUMENTS

| | | | |
|---|---|---|---|
| 3,674,648 | 7/1972 | Soli | 195/127 |
| 3,684,519 | 8/1972 | Combs | 426/1 |
| 3,767,790 | 10/1973 | Guttag | 424/81 |
| 3,860,490 | 1/1975 | Guttag | 424/81 |
| 4,053,640 | 10/1977 | Takasugi et al. | 426/1 |

*Primary Examiner*—Raymond N. Jones
*Assistant Examiner*—Elizabeth A. Hatcher
*Attorney, Agent, or Firm*—Cushman, Darby & Cushman

[57] ABSTRACT

A luminous material includes a carrier and luminous bacteria dispersed in, admixed with, confined in or applied to the carrier, the material being useful in fishery, particularly as a fish bait.

11 Claims, No Drawings

LUMINOUS MATERIAL FOR USE IN FISHERY AND METHOD FOR THE PRODUCTION THEREOF

BACKGROUND OF THE INVENTION

This invention relates to a luminous material for use in fishery which is characterized by luminous bacteria carried in or applied to a bait and also to a method for making such luminous material.

The availability of luminous baits has been widely known and artificial baits containing fluorescent substances have been already put on the market. The effectiveness of the luminous bait is generally accepted by a fact that, on inspection of the stomach of nocturnal tunnies, luminous fishes or cuttlefishes are often found in the stomach.

Thus, in order to render baits luminous, there have been proposed several methods using electric means and fluorescent substances. However, the luminescence by electrical means undesirably needs an electric supply such as a battery or cell, while the use of fluorescent substances requires an additional light source, i.e., the fluorescent substance is very short in luminescent time when placed in the dark where no light source is present. Thus, these prior methods have the fundamental and vital disadvantages.

In order to overcome these disadvantages, luminous baits have been proposed using chemical luminous substances. However, such luminous baits have a number of drawbacks, of which the toxicity of the luminous bait due to the use of the chemical luminous substances is one of the most serious problems. If, for example, one eats fishes which take the bait containing chemical luminous substances, he has a great possibility of indirectly taking the substances per se, or metabolites or decomposed products thereof. The intake of such toxic chemical substance is not favorable from a viewpoint of health.

SUMMARY OF THE INVENTION

We have made many researches for developing a luminous material or bait for use in fishery and a method for making such material. The luminous material or bait should be not only harmless, inexpensive and mass-producible but also suitably usable as a fishing bait or for fish-attracting purpose. As a result of the researches, we have succeeded in making a novel type of luminous material with the use of luminous bacteria instead of chemical substances as a luminous source, by which the drawbacks of the prior art can completely be overcome.

The present invention provides a luminous material which includes luminous bacteria carried in or applied to a carrier. The term "carrier" used herein is intended to mean baits of natural animal or plant origin which have been widely used in fishing industry, recently developed baits made of natural or synthetic polymeric materials and containers. The latter baits include artificial lures or decoys made of the polymeric materials. In particular, the baits include: fishes such as sardines, mackerel, saurels, etc.; mollusks such as cuttlefishes, octopuses, etc.; shrimps or lobsters; pupae; shellfishes; processed products obtained from fishes, mollusks, shrimps, pupae, shellfishes, such as raw fleshes, paste, minced flesh powder, etc; decoys or lures made of hydrophilic polymeric materials typical of which are those derived from alginic acid and a sodium salt thereof, carboxymethyl cellulose, etc.; containers and capsules of light-permeable polymeric materials such as polyvinyl chloride, polyvinylidene chloride, vinylon (polyvinyl alcohol), polyethylene, polypropylene, etc.; and starchy materials such as boiled rice grains, boiled noodles, boiled potatoes, boiled vermicelli, etc.

The languages "carried in or applied to a carrier" used in this specification mean "deposited on, admixed with, dispersed in and enclosed or sealed in the carrier".

The luminous material according to the invention can be applied for various purposes, e.g., as a fishing bait, a ground bait, a bait for fish culture and fish-luring material, and is particularly suitable as a bait for deep-sea and nocturnal fishes.

In addition, the luminous materials of this invention have a wide variety of applications as luminous source. For example, the luminous material can be used in the dark as an illuminator, a calling-on light, a pilot lamp, etc. Since the luminous material is usable in sea water, it may be applied as a fish-luring light. The material stands high pressure, so that it may be used in deep sea.

The luminous material of the present invention using luminous bacteria has a number of distinct advantages as bait over known fishing baits as described below.

(1) Luminous bacteria are utterly harmless to human beings, i.e., they are principally composed of proteins, carbohydrates, fats and minerals other than water and are rich in vitamin B. Fishes may take the bacteria as a nutrient and there is no fear of toxicity ascribable to the bacteria. (2) Use of luminous baits containing chemical luminous substances may result in ecological or environmental pollution. This problem on environmental pollution has been solved by using luminous bacteria instead of the chemical luminous substance. When, for example, chemical luminous substances are discharged from baits applied with such substances into sea water during use of the baits or when chemical luminous substance-containing baits which have not been taken by fishes are wasted in fishing grounds, the chemical substances may pollute the fishing grounds. In contrast, luminous bacteria originally exist in the natural world, particularly widely in sea. The bacteria have no possibility of causing environmental pollution since they are readily decomposed differently from chemical substances and are taken by planktons even if wasted in sea water.

(3) Though it seems difficult to make luminous baits of high quality by depositing chemical luminous substances on surfaces of raw baits, use of luminous bacteria makes it easy to make raw luminous baits of good quality. Because chemical luminous substances are hard to attach to or deposit on raw baits of high water content even when adhesives are added to and, if once deposited, the substances are readily separable in water by vibrations or other mechanical shocks. In contrast, luminous bacteria readily deposit on raw baits without use of any adhesives and will emit light in sea water over a long time. This is because the raw bait serves as a nutrient for the bacteria and thus the bacteria can grow on the bait surfaces. The luminous bacteria of a saprophytic type which we have isolated, have a strong tendency of depositing on raw baits satisfactorily. The combinations of the saprophytic bacteria and raw baits are one of preferred embodiments according to the invention.

(4) Some chemical luminous substances emit light, smell or taste to which fishes are not partial. The light from luminous bacteria has a tendency of rather attracting or luring fishes, and the smell or taste of the bacteria is not averse to fishes. This has been confirmed by a comparison test using chemical luminous substance-containing baits and luminous bacteria-containing baits. The luring tendency of the bacteria will be understood from the fact that luminous fishes symbiotically living with the luminous bacteria are frequently taken by fishes of bigger size.

(5) The luminous bait using chemical luminous substances is lowered in intensity of luminescence with a lapse of time and is short in time of luminescence. Though the luminous bait using luminous bacteria also tends to decrease in luminescence intensity with a lapse of time, the luminousness will be kept almost constant over a long period of time by using raw baits or by adding to the starting bait some nutrients for luminous bacteria.

(6) The chemical luminous substance-containing bait begins to emit light simultaneously with the making of the bait, the luminescence being continued during preservation. This makes it difficult to maintain the intensity of the luminescence constant in use of the bait. On the other hand, the luminous bacteria-containing bait does not give forth light during preservation when preserved in a frozen or dried state where the bacteria can live, but can emit light by defrosting or wetting.

(7) The chemical luminous substances are expensive for use as bait, whereas luminous bacteria can easily be cultivated in large amount as in the case of usual bacteria, so that they can be supplied in large amount at low cost and are thus usable as a luminous source for fishing baits.

As will be understood from the above, the baits applied with luminous bacteria have a number of merits which will not be expected from known luminous baits.

In another aspect of the present invention, there is further provided a method for the production of the luminous material described.

An object of the present invention is to provide a luminous material in which a raw or artificial bait is made luminescent by application of luminous bacteria to the bait so that fishes readily catch sight of the bait because of its luminescence.

Another object of the invention is to provide a luminous material which exhibits an increased effect of attracting fishes and are thus very suitable for use in fishery.

A further object of the invention is to provide a method for making a novel luminous bacteria-containing luminous material whereby light issued from luminous bacteria is utilizable industrially by fixation of luminous bacteria to the material.

Further objects, features and advantages will become apparent from the detailed description of the invention, which follows.

DETAILED DESCRIPTION OF THE INVENTION

The luminous bacteria usable in the present invention may be bacteria capable of bioluminescence. Most of luminous bacteria live in sea but some may live in water of a low salt content. From an ecological point of view, the luminous bacteria may be broadly classified into three groups, i.e., those floating in sea water, those parasitic on dead fish or cuttlefish, and those living symbiotically in luminous organ such as of cuttlefish or fish. In rare cases, luminous bacteria may be found to be parasitic on living insects or crustaceans.

Most of the luminous bacteria of the types just mentioned can be artificially cultivated. In taxonomical aspects, most of these luminous bacteria belong to genera, such as Pseudomonas, Photobacterium, Vibrio, Achromobacter, Micrococcus, Luchibacterium and Bacillus. Representatives of the bacteria are *Luchibacterium harveji, Photobacterium phosphoreum, Photobacterium mandapamensis, Photobacterium splendidum, Vibrio fischeri, Bacillus photogenus*, etc. However, the method of classification of the luminous bacteria differs according to the taxonomist and thus is not necessarily uniformed. Accordingly, the specific examples of the strains just mentioned are not necessarily recognized by all the bacteriologists.

The bacteria useful in the practice of the invention must be luminous bacteria capable of bioluminescence but it is out of question as to which genus or species the bacteria belong to taxonomically. In the sense, almost all of luminous bacteria which can be artificially cultivated are applicable for the luminous material according to the invention.

The luminous bacteria are easily isolated from sea water, dead fish or cuttlefish, or luminous organs of fish or cuttlefish in which they symbiotically live. In addition, luminous bacteria of certain species can be often isolated from flesh of inland animals or sausage foods which have no direct relationship with sea. As a matter of course, the bacteria may be available from microorganism collection centers located in various parts of the world. The type or kind of available microorganisms can be conveniently seen from the culture collection lists of the individual collection centers. For example, the strain of *Photobacterium phosphoreum* ATCC 11040 available from the American Type Culture Collection, which is one of the microorganism collection centers in the United States, is employable for making the fishing luminous material according to the present invention. The luminous bacteria are relatively easy to cultivate artificially, excepting a few bacteria of a specific type, and can be cultivated in large amount at a time similarly to the case of usual bacteria. The cultivation should be conducted under careful control of a sodium chloride concentration in culture medium and a cultivation temperature. In general, the luminous bacteria do not grow at all, or become very slow in growth rate when cultivated in a sodium chloride-free medium. Most of the strains grow at a relatively low temperature of 5°–20° C. However, some strains may grow in a sodium chloride-free medium or even at a temperature of as high as 37° C. The luminosity or luminousness of luminous bacteria being artificially cultivated tends to increase at the logarithmic phase of growth and to decrease at the resting stage of culture. However, the luminousness does not necessarily coincide with the phase of growth of the bacteria.

It has been found that a great many of luminous bacteria which have been isolated from the natural world will grow in nutrient media containing 3% sodium chloride, and most of the bacteria have a tendency of growing at relatively low temperatures. For instance, when a symbiotic luminous strain of *Photobacterium phosphoreum* which has been isolated from a gadoid (*Physiculus japonicus*) is inoculated in a medium (pH=7.2) containing 0.3% meat extract, 1.0% polypeptone, 3.0% sodium chloride and 0.1% glycerine, and then shake cultured in Sakaguchi's flask at 15° C. for 30 hours, the bacteria grow, rendering the entirety of the culture medium luminous. Though the luminescence is hardly recognized in the light, it has so high a brightness in the dark as to ensure reading of letters or characters of news paper.

In order to permit the luminous material or bait to emit light in use, it is essential to allow at least a part of the luminous bacteria contained in the bait to live. This is because the luminous force will disappear on extinction of the bacteria. In order to allow the bacteria to live, the bacteria are to be preserved under frozen or dried conditions similarly to the case of usual microorganisms.

The luminous bacteria are greatly different with one another, depending on the species and the strain thereof, in properties such as an intensity and color tone of luminescence, a growth rate, a nutrient requirement, a resistance to sodium chloride, resistances to low and high temperatures, an adhesiveness to fishes, a storage life, stability, etc. For example, luminous bacteria which symbiotically live on *Paratrachychthys phosthemius* have a strong resistance to low temperature, so that they are hardly damaged to the death even when frozen with dry ice. In contrast, luminous bacteria which live on *Cleidopas gloria maris* are not resistant to low temperatures and will become extinct at about 0° C. The choice of luminous material should depend on the purposes, shape, necessity of preservation and economy of the luminous material or bait for fishing. For instance, low temperature-resistant luminous bacteria are desirably used in case where the luminous material must be preserved under frozen conditions, whereas where a luminous material is of a type in which luminous bacteria are attached to or deposited on outer surfaces of the material, the bacteria are preferred to have strong adherence to a base bait and thus to be, for example, of a saprophytic type.

Aside from luminous bacteria, a variety of luminous organisms are known typical of which are luminous cuttlefishes, luminous fishes, fireflies, mushrooms, etc. According to our investigation, however, it has been found difficult that these luminous organisms other than luminous bacteria are not only cultivated in large amount, but also allowed to live in bait over a long period of time. Hence, these organisms are not suitable as the luminescent source for the luminous material of the invention.

The luminous material of this invention may take various forms depending on its end use. The content of the luminous bacteria in the luminous material also varies depending upon the purpose of usage. However, the luminous material contains the luminous bacteria in an amount sufficient to ensure illumination intensity of generally at least 0.01 lux, preferably at least 0.05 lux, most preferably at least 0.1 lux, in case of the material of 40 mm in length and 70 mm in width.

In one of the embodiments, the luminous material includes a combination of luminous bacteria with natural baits. For example, luminous bacteria are deposited, with or without growth, on outer surfaces of fishes, cuttlefishes, shrimps, shell-fishes, pupae, lobworms, earthworms, boiled potatoes, boiled noodles, boiled rice grains, etc. In the case, it is desirable to use luminous bacteria having a strong tendency to deposit. In order to deposit the bacteria on the natural bait surfaces, the bait is immersed in a culture solution of luminous bacteria for a certain time sufficient for deposition with the bacteria. If the deposition is unsatisfactory, the once deposited bait is allowed to stand in air or in a 3% sodium chloride solution to induce the surface culture. On the deposition or surface culture, the bait will be inevitably contaminated with other undesirable bacteria. However, the bait will not be contaminated to a considerable extent since the temperature and the sodium chloride concentration which are carefully controlled for the cultivation of luminous bacteria are used and the luminous bacteria are much greater in number than the contaminating bacteria. Nevertheless, it is desirable that fresh baits are used for the deposition and the deposited bait is often washed with a sodium chloride solution for the surface culture so as to keep the bait as fresh as possible.

Another embodiment of the luminous material of the invention includes a mixture of a bait of a minced or ground flesh or powder of animals or plants and luminous bacteria. In the case, the minced flesh or ground powder serves as a nutrient for the bacteria. If the bait lacks of animal components, it is desired to add a nutrient for the bacteria such as polypeptone.

A further embodiment of the luminous material includes an artificial bait containing luminous bacteria. The use of an artificial bait as a carrier is extremely desirable since edible fishes or mollusks such as cuttlefishes, sardines, etc., are not employed, leading to a saving of natural resources which gives rise to public discussion in recent years. In addition, the artificial bait can be conveniently made at low cost.

The artificial bait containing luminous bacteria can be made by a variety of methods including employing combinations of luminous bacteria and polymeric materials. Of the polymeric materials, the use of hydrophilic polymeric materials which are very similar in touch to raw baits is most preferred.

Illustrative of the polymeric materials useful in the present invention are (A) cross-linked materials of water-soluble polymers such as polyvinyl alcohol, polyvinylpyrrolidone polyacrylic acid, polymethacrylic acid, polyacryl soda, polymethacryl soda, polyacrylamide, polyethylene glycol methacrylate, polystyrene sulfonic acid, etc., (B) hydrophilic homopolymers such as polyhydroxyethyl acrylate, polyhydroxyethyl methacrylate, polydiethyleneglycol methacrylate, etc., (C) copolymers of water-soluble monomers such as hydroxyethyl acrylate, hydroxyethyl methacrylate, acrylic acid, acryl metal salts, methacrylic acid, methacryl metal salts, vinylpyrrolidone, acrylamide, diethylene glycol methacrylate, polyethylene glycol methacrylate, vinyl pyridine, styrene sulfonic acid, etc., and hydrophobic monomers such as styrene, methyl methacrylate, etc., (D) hydrophilic synthetic polymeric materials such as hydrophilic polyurethane obtained by reaction of a water-soluble polyol with a diisocyanate compound to give a reaction product (hereinlater referred to as prepolymer) and by further reaction of the prepolymer with water, and (E) hydrophilic natural polymeric materials such as those obtained by cross-linking sodium alginate, carboxymethyl cellulose or the like with divalent or multivalent metal ions such as $Ca^{2+}$, $Zn^{2+}$, $Ni^{2+}$, $Cu^{2+}$, $Sn^{4+}$, $Fe^{2+}$, $Fe^{3+}$, etc. The term "hydrophilic polymer" used herein means a polymer which is substantially insoluble in water but is capable of absorbing water in an amount of 100% or more based on the weight of the polymer of a dry state.

The luminous bacteria are applicable to polymeric materials by the following manners.

(1) To deposit luminous bacteria on surfaces of a polymeric material:

For the above purpose, the polymeric materials should be hydrophilic. Luminous bacteria do not deposit on surfaces of polymeric materials which are not hydrophilic. Hydrophilic natural polymers, particularly alginic acid cross-linked with a metal, are most preferable since luminous bacteria readily deposit on such polymers and the once deposited bacteria are hard to separate in use. The deposition of the bacteria on surfaces of hydrophilic polymeric materials is feasible by immersing the material of a suitable form in a culture solution of the bacteria. If a hydrophilic natural polymeric material is used, the bacteria may be cultivated on the surface of the material.

(2) To disperse luminous bacteria in polymeric material:

In case where the bacteria are hard to deposit on surfaces of a polymeric material or are readily separable in use even if once deposited on the surfaces, the bacteria are dispersed in the material. In this case, the polymeric material should be hydrophilic. If the polymeric material used is not hydrophilic, no luminescence occurs. Especially when there is used as hydrophilic polymer a hydrophilic natural polymer, particularly an alginic acid cross-linked with metal, the luminousness will remarkably increase. To disperse luminous bacteria in hydrophilic polymer, an aqueous solution of a water-soluble polymer is first provided and then luminous bacteria are dispersed in the aqueous solution. The polymer is subsequently rendered insoluble in water by cross-linking or other known techniques. Examples of the water-soluble polymer are polyvinyl alcohol, polyvinylpyrrolidone, polyacrylic acid, polymethacrylic acid, polyacryl soda, polymethacryl soda, polyacrylamide, polyethylene glycol methacrylate, polystyrene sulfonic acid, etc. When a hydrophilic polyurethane is used as the hydrophilic polymer, a prepolymer of the urethane is dispersed with luminous bacteria and then reached with water. Alternatively, when alginic acid or carboxymethyl cellulose each cross-linked with metal is used as the hydrophilic polymer, luminous bacteria are dispersed in an aqueous solution of sodium alginate or carboxymethyl cellulose, to which di- or multi-valent metal ions such as $Ca^{2+}$, $Zn^{2+}$, $Ni^{2+}$, $Cu^{2+}$, $Sn^{4+}$, $Fe^{2+}$, $Fe^{3+}$, etc., are added to render the polymer insoluble by cross-linking with the metal. Luminous bacteria may be cultivated in the aqueous solution of sodium alginate or carboxymethyl cellulose, to which the above-mentioned metal ions are added for the insolubilization. With polyvinyl alcohol, it will suffice that luminous bacteria are dispersed in an aqueous solution of the polymer, to which borax is added in an amount sufficient to induce the insolubilization of the polymer. Moreover, when there is used as the water-soluble polymer polyacryl soda, polymethacryl soda, polymethacryl soda, polyvinyl alcohol or polyvinylpyrrolidone, an aqueous solution of the polymer in which luminous bacteria have been dispersed may be exposed to an ionized radiation for the insolubilization in water.

The luminous bacteria used may be in the form of a culture solution or bacteria per se collected from the solution by centrifugal separation. Alternatively, the bacteria cultivated on solid media such as agar-media are also usable. In either case, the bacteria of intense luminousness in logarithmic phase are desirable.

The luminous material of this second embodiment has the following merits: (1) The material is easy to handle because of a gel-like solid; (2) No forcible aeration such as by agitation is required as in the case of culture solution since air (or oxygen) can be freely passed through the surfaces of the luminous material; (3) Though the bacteria in culture solution lose luminousness in about two days, the bacteria in the luminous material according to the invention continue to emit light over one week or more; (4) The insolubilized luminous material is usable in sea water as it is without use of any additional container; and (5) The material is shapable into any desired form depending on the purpose in end use.

(3) To confine luminous bacteria in a container made of light-permeable polymer:

The term "light-permeable" does not means complete light permeability, but a permeability of such an extent that the luminescence of the bacteria is observable from the outside of the container. The polymers usable for the above purpose are those which allow the light to permeate therethrough but are preferred to be flexible ones from a viewpoint of touch. Examples of such polymer are polyethylene, polypropylene, polyvinyl chloride, polyvinylidene chloride, vinylon, etc. The container may take any forms such as a cylinder, a pouch, a box, and a fish-like shape provided that luminous bacteria can be sealed therein. The polymer may be shaped into a desired form by any of known methods such as a blow molding, an injection molding, an injection blow molding, a vacuum forming, and a compression molding. After introduction of luminous bacteria into the container, the container is hermetically sealed by a heat or supersonic sealer or by adhesion with adhesives or by covering with suitable means.

The artificial baits may be further applied with a fish attractant capable of attracting fishes with only small amount of the attractant by stimulation of the organ of smell of fishes. The attractant usable for the above purpose is, for example, a material called "soluble" obtained by grinding and then autodigesting or enzymatically decomposing the internal organs of animals, fish meal, minced fish flesh, cuttlefish oil or the like. Further, addition, to the luminous bacteria, of a nutrient such as meat extract, polypeptone or yeast extract which is usually employed for fermentation of microorganisms will give a remarkable effect on maintenance of the luminescence of the bacteria.

(4) To cover luminous bacteria deposited on bait with polymer film:

After deposition of luminous bacteria on surfaces of known baits such as cuttlefishes, sardines, mackerel pike, shrimps, shellfishes, lobworm, and boiled potatoe, noodle and rice, the deposited bait is covered with a film of hydrophilic polymer so as to prevent the bacteria from being separated from the bait surfaces. The covering with a film of hydrophilic polymer is feasible, after deposition of the bacteria on the bait surfaces, by applying an aqueous solution of a water-soluble polymer or a prepolymer of urethane onto the bait and then subjecting the applied polymer to a cross-linking treatment or subjecting the prepolymer to reaction with water for insolubilization.

The following examples further illustrate the present invention.

EXAMPLE 1

Luminous bacteria of a saprophytic type which had been previously isolated from a horse-mackerel purchased at the fish market were inoculated in a medium of pH of 7.2 containing 0.3% meat extract, 1.0% polypeptone, 0.1% glycerine and 3.0% sodium chloride and shake cultured at a temperature of 15° C. for 36 hours.

A fresh mackerel pike, horse-mackerel, mackerel, sardine, minced flesh of sardine, shrimp, shucked short-necked clam and cuttlefish which were separately got in the fish market were all washed well with a 3% sodium chloride solution and then immersed in the culture solution maintained at 15° C. for 3 hours. After gently shaking, the fishes and cuttlefish were withdrawn from the culture solution and allowed to stand in air at 15° C. for 24 hours, followed by propagating the bacteria on the surfaces of each of the fishes and cuttlefish to give luminous materials for fishing purpose.

EXAMPLE 2

Luminous bacteria of *Photobacterium phosphoreum* ATCC 11040 procured from the American Type Culture Collection were innoculated in a medium of pH of 7.0 containing 1.0% polypeptone, 0.1% mannose, 0.1% glycerol, 0.3% meat extract and 5.0% sodium chloride and shake cultured at 15° C. for about 30 hours to obtain 100 ml of a culture solution in which the bacteria grew and emitted light. To 50 ml of the culture solution was added a small amount of a fish oil as a fish-attracting substance, which was then mixed with 50 ml of an aqueous 10% sodium alginate solution and agitated. The mixture was placed in an aqueous 0.5 mol calcium chloride solution and allowed to stand for about 20 minutes to fix the bacteria. The solidified mass was cut into pieces of a desired size to give a luminous material or bait.

EXAMPLE 3

Luminous bacteria of *Photobacterium phosphoreum* symbiotically living on a gadoid (*Physiculus japonicus*) were isolated and innoculated in a medium of pH of 7.2 containing 0.3% meat extract, 0.1% malic acid, 1.0% polypeptone, 0.1% glycerol and 3.0% sodium chloride, followed by cultivating at 20° C. for 24 hours in a jar fermenter. To 1 l of the culture solution were added a small amount of fish oil, 1 g of meat extract, 3.0 g of polypeptone and 0.3 g of glycerol. Then, the procedure of Example 2 was repeated thereby giving a luminous material. This luminous material had a more intense luminousness than that obtained in Example 2. The luminous material stopped giving forth light when preserved in a frozen state of −15° C. for 1 month, but was again turned luminous on defrosting. The luminousness hardly changed when the material was placed in sea water.

EXAMPLE 4

Boiled rice grains, boiled noodle, boiled vermicelli, pupae, and paste of boiled noodle were introduced into a culture solution as obtained in Example 3. 3 hours after the introduction, they were withdrawn from the solution to obtain luminous materials for fishing.

EXAMPLE 5

Luminous bacteria isolated from a cuttlefish purchased at the fish market were innoculated in a medium of pH of 7.2 containing 0.3% meat extract, 1% polypeptone, 0.1% glycerine and 3% sodium chloride and shake cultured at a temperature of 15° C. 20 hours after commencement of the cultivation, the solution was made luminous to an extent. 200 ml of the solution was added with 8 g of sodium alginate and well agitated to completely dissolve the alginate therein. The mixture was placed in an aqueous 0.4 mole $CaCl_2$ solution in a desired form, followed by allowing to stand at room temperature for 1 hour for insolubilization to give a gel-like luminous material. The gel contained about 1000% of water based on a dry weight of the gel.

The luminous gel was so luminous as to be well recognizable in the dark. When allowed to stand in sea water of 10° C. for 1 week, the luminous gel continued to emit light with the luminousness or luminous intensity being hardly lowered.

When the above procedure was repeated using $NiCl_2$ instead of $CaCl_2$, similar results were obtained.

EXAMPLE 6

A strain of luminous bacteria of *Photobacterium phosphoreum* ATCC 11040 procured from the American Type Culture Collection was innoculated in a medium of pH of 7 containing 1% polypeptone, 0.1% mannose, 0.1% glycerol, 0.3% meat extract and 3% sodium chloride and shake cultured at 15° C. for about 24 hours to obtain 100 ml of a luminous culture solution in which the strain grew. To the solution was added 4 g of sodium alginate, followed by repeating the procedure of Example 5 to give a gel-like luminous material. When allowed to stand in sea water of 10° C. for 5 days, the luminous gel continued to emit light with the luminousness being hardly lowered.

EXAMPLE 7

Luminous bacteria of *Photobacterium phosphoreum* symbiotically living on a gadoid (*Physiculus japonicus*) were isolated and this strain was innoculated in a medium of pH of 7.2 containing 0.3% meat extract, 0.1% malic acid, 1% polypeptone, 0.1% glycerol and 3% sodium chloride, followed by cultivating under agitation at 20° C. for 24 hours in a jar fermenter. The resulting culture solution was divided into portions each in 200 ml, to which were added 8 g of sodium alginate, 8 g of polyacrylic soda, 8 g of polymethacryl soda, 8 g of carboxymethyl cellulose, 2 g of alginic acid, 2 g of polyacrylic acid and 2 g of polymethacryl acid, respectively. With the solutions added with the alginic acid, polyacrylic acid and polymethacryl acid, an aqueous sodium hydroxide solution was added to each of the solutions to adjust its pH to 7. Thereafter, the procedure of Example 5 was repeated for each of the solutions to give gel-like luminous materials. All of the materials emitted light, of which the gel-like material using sodium alginate had the most intense luminousness.

EXAMPLE 8

200 ml of a culture solution as obtained in Example 7 was subjected to a centrifugal separation to collect the bacteria. The thus collected bacteria were suspended in an aqueous solution of 3% sodium chloride and 5% sodium alginate. Then, the procedure of Example 5 was repeated to give a luminous material. This material had almost the same luminousness as that of Example 7 using sodium alginate but was inferior in continuation of the luminescence.

EXAMPLE 9

200 ml of a culture solution as obtained in Example 3 was added with 3 g of polyvinyl alcohol for dissolution, which was then placed in an aqueous 5% borax solution, followed by allowing to stand at room temperature for 2 hours for insolubilization to give a gel-like luminous material.

EXAMPLE 10

100 ml of a culture solution as obtained in Example 5 was added with 4 g of polyvinyl alcohol for dissolution, divided into several portions, and allowed to stand at −10° C. for 3 hours for insolubilization. The resulting gels were not luminous but emitted light after allowed to stand at room temperature for a while.

These gels contained water in amounts of 500% or more based on dry weights of the respective gels. All of the gels remained luminous in sea water over not less than 5 days.

EXAMPLE 11

200 ml of a culture solution as obtained in Example 7 was subjected to a centrifugal separation to collect the bacteria. The thus collected bacteria were suspended in an aqueous solution of 3% sodium chloride and 5% sodium alginate, followed by repeating the procedure of Example 5 to give a gel-like luminous material. This gel contained about 300% of water based on a dry weight of the gel. The luminous gel had the almost the same luminousness as that of Example 7 using sodium alginate.

EXAMPLE 12

200 ml of a culture solution as obtained in Example 7 was provided and added with 3 g of polyvinyl alcohol for dissolution. The solution was placed in an aqueous 3% borax solution and allowed to stand at room temperature for 2 hours for insolubilization to give a gel-like luminous material. The material continued luminous over not less than 1 week when placed in an aqueous 3% sodium chloride solution of 10° C.

EXAMPLE 13

100 ml of a culture solution as obtained in Example 5 was added with 4 g of polyvinyl alcohol for dissolution and allowed to stand at −20° C. for 3 days, followed by treating at room temperature for 10 hours to obtain a gel-like luminous material. The thus obtained gel contained about 1500% of water based on a dry weight of the gel.

EXAMPLE 14

10 g of polyvinyl alcohol and 3 g of sodium chloride were dissolved in 100 ml of water. Luminous bacteria of the same type as used in Example 4 were suspended in the solution and exposed to a γ ray (cobalt 60) at 3 Mrad. in an atmosphere of nitrogen to give a gel-like luminous material. The gel contained about 1600% of water based on a dry weight of the gel and continued luminous in sea water of 10° C. for 1 week.

EXAMPLE 15

The luminous material obtained by the same method as in Example 5 was placed in each of artificial baits of a cylindrical form having an inner diameter of 10 mm and a height of 80 mm. These baits were for the fishing of cuttlefish and were made of polyvinyl chloride, vinylon, polyethylene and polypropylene, respectively. Then, each of the cylinders was hermetically sealed to obtain artificial luminous baits. Similarly, the above procedure was repeated using a known fluorescent substance to give an prior art artificial luminous bait. When these baits were placed in the dark at room temperature, it was found that the luminescence from the known bait disappeared in 5 minutes, while the bait of the invention using the luminous bacteria was hardly lowered in luminousness even when allowed to stand for 3 days. The illumination intensity of the respective artificial baits were measured by means of an illuminometer. The test results are shown below.

Table 1

| | Luminousness of the Baits in the Dark | |
|---|---|---|
| time (min) | known artificial bait using fluorescent substance (lux) | artificial bait of the invention using luminous bacteria (lux) |
| 0 | 0.31 | 0.38 |
| 1 | 0.04 | 0.36 |
| 5 | 0.01 | 0.37 |
| 120 | 0 | 0.34 |
| 240 | 0 | 0.35 |
| 3 days | 0 | 0.31 |

EXAMPLE 16

The luminous materials obtained in Examples 1 and 4 were used to effect the following test. The materials were used to angle for bottom fishes e.g., scorpionfish, rockfish, grunt, etc., at depths of 200–250 m. The test was conducted for about 5 hours by two testers in each test area, each using a rod with six hooks to be baited with the luminous materials or raw materials. The test was repeated three times, with the test results, shown below, being the average, in number of fishes caught, of the three tests.

Table 2

| Bottom Fishing Test Results | |
|---|---|
| Kind of bait | Total number of fishes (caught by two testers) |
| raw mackerel pike | 5 |
| luminous mackerel pike | 7 |
| raw horse-mackerel | 4 |
| luminous horse-mackerel | 9 |
| raw mackerel | 6 |
| luminous mackerel | 19 |
| raw sardine | 4 |
| luminous sardine | 7 |
| raw cuttlefish | 8 |
| luminous cuttlefish | 21 |
| raw shrimp | 5 |
| luminous shrimp | 8 |
| shucked short-necked clam | 4 |
| luminous shucked short-necked clam | 8 |
| minced flesh of sardine | 5 |
| luminous minced flesh of sardine | 6 |
| boiled rice grains | 3 |
| luminous boiled rice grains | 5 |
| boiled noodle | 2 |
| luminous boiled noodle | 3 |
| boiled vermicelli | 1 |
| luminous boiled vermicelli | 2 |
| pupae | 3 |
| luminous pupae | 5 |
| paste of boiled noodle | 2 |
| luminous paste of boiled noodle | 3 |

EXAMPLE 17

The gel-like luminous materials of a sausage form obtained in Examples 7 and 9 were used as bait to conduct the following test. 1,000 palaemon paucidens were placed in a concrete water tank of 4 m in length, 1.5 m in width and 1 m in water depth. Two pots or traps of a conical form (having diameters of 100 cm and 60 cm at the bottom of the top thereof, respectively) were set on the bottom of the tank. Then, a slice of herring was suspended in one of the pots and a slice of herring and the luminous material was suspended in the other pot. The test was conducted during the night and the number of the paucidens trapped in the pot every two hours were counted. The test was repeated three times. The test results shown in Table 3 below are the average, in number of the trapped paucidens, of the three experiments.

Table 3

Effect of Luminous Material On Palaemon Paucidens

| Kind of bait | Number of palaemon paucidens trapped |
|---|---|
| raw herring | 14 |
| raw herring + luminous sodium alginate | 26 |
| raw herring | 13 |
| raw herring + luminous polyacryl soda | 17 |
| raw herring | 15 |
| raw herring + luminous polymethacryl soda | 19 |
| raw herring | 13 |
| raw herring + luminous carboxymethyl cellulose | 22 |
| raw herring | 14 |
| raw herring + luminous polyvinyl alcohol | 21 |

EXAMPLE 18

The artificial luminous baits for angling for cuttlefish made in Example 15 were used to effect the following test. The test was conducted for 3 hours to angle for black cuttlefish by two testers in each test area by use of rods each having five hooks applied with the artificial baits. The test was conducted three times. The test results, shown in Table 4 below, are the average, in number of the angled cuttlefish, of the three tests.

Table 4

Effect of Artificial Luminous Baits on Cuttlefish

| Type of artificial bait | Number of cuttlefish (caught by two testers) |
|---|---|
| non-luminous artificial bait (commercially available) | 20 |
| fluorescent substance-contained artificial bait (commercially available) | 24 |
| artificial luminous bait using polyvinyl chloride container | 27 |
| artificial luminous bait using polyvinylidene chloride container | 36 |
| artificial luminous bait using vinylon container | 34 |
| artificial luminous bait using polyethylene container | 29 |
| artificial luminous bait using polypropylene container | 39 |

EXAMPLE 19

Luminous mackerels or cuttlefishes obtained in Example 1 were applied to 600 hooks of a tunny-fishing ship as well as raw mackerels or cuttlefishes. The test was repeated three times with the following results.

Table 5

| Kind of bait | Effect on Tunny | | |
|---|---|---|---|
| | Test No. | Raw bait | Luminous bait |
| cuttlefish | 1 | 12* | 18 |
| | 2 | 9 | 15 |
| | 3 | 13 | 21 |
| mackerel | 1 | 11 | 14 |

Table 5-continued

| Kind of bait | Effect on Tunny | | |
|---|---|---|---|
| | Test No. | Raw bait | Luminous bait |
| | 2 | 12 | 17 |
| | 3 | 8 | 13 |

(Note)
The values in the Table mean the number of caught tunnies per 600 hooks.

EXAMPLE 20

The luminous material of the sausage form (with a diameter of 2 cm and a height of 7 cm,) obtained in Example 7, using sodium alginate was used to effect a crab catch test. 40 crab pots having diameters of 150 cm and 100 cm at the bottom and top thereof, respectively, were provided, 20 pots for control being introduced with raw pollack and the other 20 pots being introduced with raw pollack and the luminous material. These pots were placed on the sea bottom for 3 days and withdrawn to count for a total number of caught crabs, from which the number of crabs per pot was calculated. The test was repeated three times. The test results, shown in Table 6 below, are the average of the three tests.

Table 6

| Crab Catch Test | | Chionoecetes opilio | Paralithodes camtschatica |
|---|---|---|---|
| raw pollack | total number | 401 | 99 |
| | number per pot | 20 | 5 |
| raw pollack and luminous material | total number | 540 | 174 |
| | number per pot | 27 | 9 |

We claim:

1. A method for the production of a luminous fishing article, comprising:
   providing an aqueous solution containing a water-soluble polymer;
   dispersing luminous bacteria in said solution; and
   insolubilizing the polymer under conditions which maintain at least a part of the bacteria alive.

2. The method according to claim 1, wherein the water-soluble polymer is a natural polymer and wherein said insolubilization is effected by mixing divalent or multivalent metal ions with the dispersion.

3. The method according to claim 2, wherein said natural polymer is alginic acid, sodium alginate, carboxy-methylcellulose or a salt thereof.

4. The method according to claim 3, wherein said metal ions include $Ca^{2+}$ or $Ni^{2+}$.

5. The method according to claim 1, wherein the water-soluble polymer is a synthetic polymer.

6. The method according to claim 5, wherein said synthetic polymer is polyacrylic acid, polymethacrylic acid or a salt thereof, and wherein said insolubilization is effected by mixing metal ions of divalent or more with the dispersion.

7. The method according to claim 6, wherein said metal ions include $Ca^{2+}$ or $Ni^{2+}$.

8. The method according to claim 5, wherein said synthetic polymer is polyvinyl alcohol, and wherein said insolubilization is effected by mixing borax with the dispersion.

9. The method according to claim 5 wherein said synthetic polymer is polyvinyl alcohol, and wherein said insolubilization is effected by freezing said dispersion and thawing the frozen dispersion.

10. The method according to claim 5 wherein said insolubilization is by an ionized radiation.

11. A luminous fishing article produced by the method of claim 1.

* * * * *